United States Patent [19]

Huber et al.

[11] Patent Number: 5,426,198

[45] Date of Patent: Jun. 20, 1995

[54] 9α-DEHALOGENATION PROCESS

[75] Inventors: Joel E. Huber, Kalamazoo; Jeffrey A. Fleming, Augusta, both of Mich.

[73] Assignee: The Upjohn Company, Kalamazoo, Mich.

[21] Appl. No.: 460,842

[22] Filed: Jan. 31, 1990

Related U.S. Application Data

[63] Continuation-in-part of Ser. No. 95,803, Sep. 11, 1987, abandoned, which is a continuation-in-part of Ser. No. 85,907, Aug. 14, 1987, abandoned.

[51] Int. Cl.⁶ .............................................. C07J 1/00
[52] U.S. Cl. ..................................... 552/621; 552/619; 552/622
[58] Field of Search ................. 260/397.45, 397.47; 552/505, 566, 572, 574, 576, 577, 616, 621, 622, 619; 540/119, 63

[56] References Cited

U.S. PATENT DOCUMENTS 3,480,622  11/1969  Barton ............................. 260/397.45
4,304,727  12/1981  Heather et al. .................. 260/397.45
4,325,881  4/1982  Heather et al. .................. 260/397.45

OTHER PUBLICATIONS

Castro, et al JACS vol. 85, 1963 pp. 2768 to 2773.
Graber, et al Chemical Abstracts vol. 109, 1988 Abstract 38061c.
Barton et al. JACS 88(13) 1966 pp. 3016-3021.
Robinson et al. J. Org. Chem. 31, 1966 pp. 2749-2756.
Djerassi, Steroid Reactions, Holden Day Inc. San Francisco, 1963 pp. 249-251.
Levine, et al. JACS, vol. 81, 1959 pp. 2826-2829.
D. H. R. Barton, et al., "A synthesis of 11β-Hydroxy-Steroids", 1964, Tetrahedron Letters 43:3151-3153.

Primary Examiner—Nicholas Rizzo
Attorney, Agent, or Firm—Bruce Stein

[57] ABSTRACT

The present invention involves improved processes for the dehalogenation of 9α-halosteroids (I)

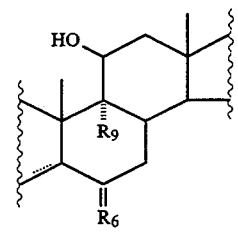

to produce the corresponding 11β-hydroxy steroids (II)

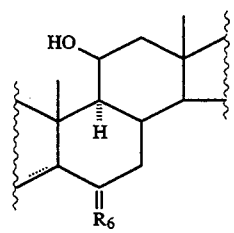

which are known to be useful as pharmaceutical, where the improvements comprise (1) adding the 9α-halo steroid (I) to the chromium and (2) using catalytic amounts of chromium in the presence of a means of converting chromium (II) to chromium (III).

19 Claims, No Drawings

9α-DEHALOGENATION PROCESS

CROSS-REFERENCE TO RELATED APPLICATIONS

The present patent application is a continuation-in-part (national phase) application of PCT patent application PCT/US88/02430 filed Jul. 22, 1988 which is a continuation-in-part application of U.S. patent application Ser. No. 07/095,803, filed Sep. 11, 1987 (now abandoned) which is a continuation-in-part application of U.S. patent application Ser. No. 07/085,907, filed Aug. 14, 1987 (now abandoned).

BACKGROUND OF THE INVENTION

1. Field of the Invention

The present invention involves improved processes for the dehalogenation of a 9α-halosteroids (I) to produce the corresponding 11β-hydroxy steroids (II) which are known to be useful as pharmaceuticals.

2. Description of the Related Art

11β-Hydroxy steroids, especially corticoids, are very important commercial steroids. These can generally be made two ways; first by fermentation with a microorganism which will hydroxylate at the 11 position in the β configuration and second by starting with a $\Delta^{9(11)}$-steroid, forming the halohydrin and then dehalogenating. Processes for dehalogenation of 9α-halo-11β-hydroxy steroids are known.

U.S. Pat. No. 3,480,622 discloses a process for the debromination of a 9α-bromo-11β-hydroxy steroid by reaction of the brominated steroid with a salt of a polyvalent metal (chromium) in which the metal is transformed from a lower oxidation state (+2) to a higher state (+3) in the presence of a compound capable of providing hydrogen radicals preferably a thiol. U.S. Pat. No. 3,480,622 discloses that the metal reducing agent, preferably chromous acetate, is "... present in at least stoichiometric quantities with respect to the steroid and is advantageously in excess. 1 to 10 moles of reducing agent may, for example, be used, preferably about 5 mole." Further, that "The reaction temperature does not appear to be critical . . . " −50° to 100° being operable and 20°–25° is convenient. While no order of addition of reactants is taught, in the specification, in all the examples the metal reducing agent, chromous acetate, was added to the 9α-bromo steroid. This patent states the claimed process gives yields of 75–80%. U.S. Pat. No. 3,480,622 discloses four examples. Two examples are to 11β-fluoro steroids. The two other examples, examples 10 and 14(b), involve 11β-hydroxy functionality in the C-ring, having $\Delta^{1,4}$-3-keto functionality in the steroid A-ring and gave yields of 70 and 80% respectively. US patent did not recycle the chromium (III) produced by the dehalogenation to chromium (II), hence at least one equivalent of chromium (II) was required. Preferred was 5 equivalents.

U.S. Pat. Nos. 4,304,727 and 4,325,881 improved upon the process of U.S. Pat. No. 3,480,622 by using thioglycolic acid as the thiol (hydrogen radical source). These two patents teach (with the exception of Example 7 in both patents) that the chromous ion should be present in "A slight excess over theory . . . ." These two patents also state "Temperature is not critical, −50° to 100° being suitable, 20°–50° being preferred." These two patents like U.S. Pat. No. 3,480,622 also do not mention the order of addition of reactants in the non-example portion of the specification. However, like U.S. Pat. No. 3,480,622, in the EXAMPLES these patents disclose only the addition of the chromous ion to the 9α-bromo steroid. The process in these patents did not recycle the chromium (III) produced by the dehalogenation to chromium (II), hence the requirement that a slight excess over theory, at least one equivalent of chromium (II), be used. Example 7 of U.S. Pat. Nos. 4,304,727 and 4,325,881 used 0.21 equivalents of chromium and reported a chemical yield of 83%. It has been found that the yield obtained in Example 7 of U.S. Pat. Nos. 4,304,727 and 4,325,881 was due to the zinc present and not the chromium which was not soluble under those conditions, compare EXAMPLES 6 and 7 in CHART B.

Tetrahedron Letters 43, 3151 (1964) [BARTON I] discloses that 9α-bromoprogesterone can be debrominated using 5 equivalents of chromous acetate at room temperature in 6–13 hr in 80% yield. Similarly, the $\Delta^{1,4}$-steroid, 9α-bromoprednisolone 21-acetate was debrominated in 74% yield.

J. Am. Chem. Soc., 88, 3016 (1966) [BARTON II] and J. Org. Chem., 31, 2749 (1966) [BARTON III] propose mechanistic interpretations of the results of BARTON I and additional studies of chromous ion reductions.

The processes of the present invention dehalogenate 9α-halo steroids in >90% conversion by (1) adding the steroid to the chromium ion rather than adding the chromium ion to the steroid and (2) using <1 equivalent of soluble chromium ion in the presence of a means for converting chromium (III) to chromium (II).

SUMMARY OF INVENTION

Disclosed is a process for the preparation of an 11β-hydroxy steroid of formula (II) where which comprises (1) contacting a 9α-halo steroid of formula (I) where $R_9$ is —Cl or —Br with <1 equivalent of soluble chromium ion, a hydrogen radical source and a means for reducing the chromium (III) to chromium (II).

Also disclosed is a process for the preparation of an 11β-hydroxy steroid of formula (II) which comprises (1) adding a 9α-halo steroid of formula (I) where $R_9$ is —Cl or —Br to a mixture of soluble chromium ion, a hydrogen radical source and a means for reducing chromium (III) to chromium (II).

Preferred is a process where the 9α-halo steroid (I) is of the formula (IA) where ⋯ is a single or double bond; $R_6$ is α-$R_{6-1}$:β-$R_{6-2}$, where one of $R_{6-1}$ and $R_{6-2}$ is —H and the other is —H, —F or —CH$_3$;

(D-I) $R_{16}$ is α-$R_{16-1}$:β-$R_{16-2}$ where one of $R_{16-1}$ and $R_{16-2}$ is —H and the other is —H, —OH or —CH$_3$ and $R_{17}$ is

=O,

α—H:β—CO—CH$_3$,

α—OR$_{17-5}$:β—CO—CH$_3$ where R$_{17-5}$ is —H, —CO—R$_{17-51}$ where R$_{17-51}$ is C$_2$—C$_4$ alkyl or φ optionally substituted with 1 or 2 —OCH$_3$, α—OR$_{17-1}$:β—CO—CH$_2$—OR$_{21-1}$ where R$_{17-1}$ is —H or —CO—R$_{17-2}$ where R$_{17-2}$ is C$_1$—C$_3$ alkyl or φ and where R$_{21-1}$ is —H or —CO—R$_{21-2}$, where R$_{21-2}$ is C$_1$—C$_3$ alkyl or φ optionally substituted with —Cl or —NO$_2$, α—OR$_{17-3}$:β—CN where R$_{17-3}$ is

—H,

THP,

—CH$_2$—OCH$_3$,

—CHR$_{17\text{-}31}$—O—R$_{17\text{-}32}$ where R$_{17\text{-}31}$ is C$_1$—C$_3$ alkyl and R$_{17\text{-}32}$ is C$_1$—C$_4$ alkyl or $\phi$ and —SiR$_{17\text{-}33}$R$_{17\text{-}34}$R$_{17\text{-}35}$ where R$_{17\text{-}33}$ R$_{17\text{-}34}$ and R$_{17\text{-}35}$ are the same or different and are selected from the group consisting of C$_1$—C$_4$ alkyl, C$_1$—C$_4$ alkoxy, C$_1$—C$_4$ monohaloalkyl where halo is —Br or —Cl, $\phi$ optionally substituted with 1 or 2 —OCH$_3$ or —NH$_2$;

(D-II) the 16,17-acetonide of a compound where R$_{16\text{-}1}$ is —OH, and where R$_{17}$ is $\alpha$—OR$_{17\text{-}1}$:$\beta$—CO—CH$_2$—OR$_{21\text{-}1}$ where R$_{17\text{-}1}$ is —H where R$_{21\text{-}1}$ is as defined above.

DETAILED DESCRIPTION OF THE INVENTION

U.S. Pat. Nos. 3,480,622, 4,304,727 and 4,325,881 as well as the above journal articles describe dehalogenation processes of 9$\alpha$-halo-11$\beta$-hydroxy steroids.

In addition to the absolute yield of the 11$\beta$-hydroxy steroid (II) being important, the ratio of the 11$\beta$-hydroxy steroid (II) the corresponding undesired $\Delta^{9(11)}$ steroid is very important. Even if the yield of a particular process is less than the yield of another process, the process with the lower yield may be more valuable if the ratio 11$\beta$-hydroxy/$\Delta^{9(11)}$ is more favorable due to the difficulty in some cases of removing the $\Delta^{9(11)}$ compound from the 11$\beta$-hydroxy product (II). The processes of the present invention not only produces the 11$\beta$-hydroxy steroid (II) in very high conversion but also with a very good ratio of 11$\beta$-hydroxy steroid (II) to $\Delta^{9(11)}$ steroid.

All the references discussed in the Description of the Related Art teach that the chromium mixture should be added to the 9$\alpha$-halo steroid (I). It has been discovered that the ratio of 11$\beta$/$\Delta^{9(11)}$ can be improved by reversing the order of addition and adding the 9$\alpha$-halo steroid (I) last, see Table 1 in CHART B, that is, adding the 9$\alpha$-halo steroid (I) to the chromium mixture rather than the chromium mixture to the 9$\alpha$-halo steroid (I). Further, it has been discovered that it is best to add the steroid slowly, preferably over a period of at least 1 min, more preferably over a period of at least 5 min, even more preferably over a period of at least 15 min.

It also has been discovered that the chemical yield and ratio of 11$\beta$/$\Delta^{9(11)}$ can be improved by using a catalytic amount, less than one equivalent of soluble chromium ion, in the presence of a means for converting the chromium (III) produced by the dehalogenation reaction to the chromium (II) required for the dehalogenation reaction. The catalytic amount of chromium must be soluble in the reaction mixture. While Water can be used to solubilize the chromium ion, it is preferable not to use water for operational reasons. Hence, while chromium sulfate is insoluble (for all practical purposes) in DMF, chromium chloride is soluble in DMF and therefore it is preferred to use chromium chloride in DMF without water than to use chromium sulfate solubilized by water in DMF. The insolubility of chromium sulfate in DMF is the reason why Example 7 of U.S. Pat. Nos. 4,304,727 and 4,325,881 gave 83% yield and in a repeat experiment gave 78% (see EXAMPLE 6 in Table 1, CHART B). The same reaction mixture without any chromium gave 81.9% (see EXAMPLE 7 in Table 1, CHART B). Soluble as used in this patent does not refer to theoretical solubility where a solute may be finitely and infinitesimally soluble in a solvent, but rather refers to practical, useful or sufficiently soluble as normally used by one skilled in the art.

By this definition, salt (sodium chloride) is not soluble in gasoline but soluble in water even though sodium chloride has a very small (but finite) solubility in gasoline. Less than 1 equivalent of chromium ion provides the 11$\beta$-hydroxy steroid (II) in >90% conversion and produces <10% of the undesired corresponding $\Delta^{9(11)}$ side reaction product.

The processes of the present invention requires a 9$\alpha$-halo steroid (I), soluble chromium ion, a hydrogen radical source and a means for recycling chromium (III) to chromium (II).

The processes of the present invention require the halohydrin 9$\alpha$-chloro-11$\beta$-hydroxy or 9$\alpha$-bromo-11$\beta$-hydroxy substitution in the steroid B and C rings. Other substitution in the A and D rings is operable. For example in the steroid A ring, $\Delta^4$-3-keto, $\Delta^{1,4}$-3-keto, 3$\beta$-hydroxy-$\Delta^5$-, 3-hydroxy-reduced A ring functionality is operable. In the steroid D ring, known substitution at C$_{16}$ and C$_{17}$ is operable including 16-alkyl, 16-methylene, 16-fluoro, 16-hydroxy. At C$_{17}$ progesterone, hydroxyprogesterone, cyanohydrin, corticoid and androstane side chain substitution is operable.

The 9$\alpha$-halo steroids (I) include the 9$\alpha$-halo steroids (IA) which are known to those skilled in the art or can be readily prepared from known compounds by means known to those skilled in the art. It is preferred that R$_9$ be —Br. The 9$\alpha$-halo steroids (I) include both $\Delta^4$-3-keto steroids (⎯ is a single bond) and ⎯ is a double bond). With the $\Delta^4$-3-keto steroids, various C$_3$protectedforms are deemed equivalent to the parent or free $\Delta^4$-3-keto form. Further, various C$_3$ hydroxy compounds such as 3$\beta$-hydroxy, 3$\beta$-hydroxy-$\Delta^5$- are deemed equivalent to the since they can be readily converted to each other.

While U.S. Pat. Nos. 3,480,622, 4,304,727 and 4,325,881 all disclose the dehalogenation of 9$\alpha$-halo $\Delta^4$-3-keto and $\Delta^{1,4}$-3-keto steroids, BARTON I, II and/or III clearly points out the increased difficulty with dehalogenating 9$\alpha$-halo $\Delta^{1,4}$-3-keto steroids, see pages 2749–2750 of BARTON III. U.S. Pat. Nos. 4,304,727 and 4,325,881 disclose dehalogenation of $\Delta^{1,4}$-3-keto steroids in Examples 3 and 4, both of which are write-in examples. U.S. Pat. No. 3,480,622 discloses dehalogenation of $\Delta^4$-3-keto steroids in Examples 10 and 14(b). The chemical yields of these examples are only 74 and 80% respectively. By using a slow addition of the halohydrin to the chromium mixture and/or catalytic amounts of soluble chromium ion in the presence of a means for transforming chromium (III) to chromium (II), the conversion of dehalogenating a 9$\alpha$-halo-$\Delta^{1,4}$-3-keto steroid is increased to >90%.

Chromium ion in the above references has been referred to as chromium (III), chromic salt, chromic ion, etc. Either chromium (II) or chromium (III) is operable. The term chromium ion as used in this patent includes both chromium (II) and chromium (III). Chromium (II) is the active species and is operable, but it is preferred that the chromium be chromium (III).

The above references teach that various salts of chromium such as the acetate, chloride, and sulfate are the preferred salts. The salt must be soluble in the solvent(s) used and therefore any soluble chromium salt is operable. If the salt is not soluble in the solvent(s) used, a sufficient amount of water should be added to solubilize the chromium salt. However, as stated above it is preferred not to add water. Suitable chromium salts include the sulfate, chloride, acetate, fluoride, hydroxide, K$_2$Cr$_2$(SO$_4$)$_4$ and nitrate. Preferred are the sulfate and chloride, most preferred is the chloride.

All the above US Patents teach that at least a stoichiometric amount of chromium is needed. U.S. Pat. Nos. 4,304,727 and 4,325,881 teach that a slight excess over theory is preferred, while U.S. Pat. No. 3,480,622 teaches that 1–10 moles is preferred, 5 moles being more preferred. It has been discovered that catalytic amounts (<1 equivalent) of chromium are operable, and even preferable, if the chromium salt is soluble. The amount of chromium needed varies with the amount of oxygen present and usually varies inversely with the scale of the reaction mixture. On small bench scale 1 equivalent may be necessary. EXAMPLES 6–15 utilized 0.2 equivalents and at a scale of 60–70 kg of 9α-halo steroid (I), only 0.04 equivalents are needed.

Hydrogen radical sources include, for example, hypophosphorous acid, 1,4-dihydrobenzene, 1-benzyl-1,4-dihydronicotinamide, cyclopentadiene, catechol, thiols, H—Si—(R)$_3$ where the R's are the same or different and are selected from the group consisting of C$_1$—C$_4$ alkyl and $\phi$ optionally substituted with 1 or 2 —OCH$_3$, and H—Sn—(R)$_3$ where R is as defined above. It is preferred that the hydrogen radical source be a thiol. Thiols include compounds of the formulas R$_t$—SH. It is preferred that R$_t$ be —CH$_2$—COOH or —CH$_2$CH$_2$—COOH; it is more preferred that the thiol be thioglycolic (thiovanic) acid where R$_t$ is —CH$_2$—COOH. Improved chemical yields result from the use of greater than 1 equivalent of the thiol, preferably from about 1.5 to about 3.0 equivalents.

The chromium (III) can be recycled to chromium (II) as is known to those skilled in the art. The means for recycling chromium (III) to chromium (II) includes zinc, magnesium, zinc amalgam and magnesium amalgam. Preferred is zinc and magnesium; most preferred is zinc. It is preferred that when the means for recycling is zinc it be present as zinc dust.

Aprotic solvents and alcohols of the formula R$_a$—OH where R$_a$ is C$_1$—C$_4$ and mixtures thereof are operable. It is necessary that the solvent or solvent mixture be such that the chromium salts are soluble therein. If not, sufficient water should be used as a cosolvent to solubilize the chromium. Suitable aprotic solvents include DMF, DMAC, acetone, methylene chloride, THF, acetonitrile, DMI, DMSO and mixtures thereof. Alcoholic solvents include methanol, ethanol, isopropanol and butanol. Preferred is DMF and DMSO.

The same references teach that temperature is not critical, that temperatures between about −50° to about 100° are operable and preferred is about room temperature (20°–25°) or up to about 50°. Better results can be obtained if the temperature is maintained between −10° and 30°.

While various temperature ranges, equivalents of chromium and solvents ate set forth above, it must be realized that the particular temperature, equivalents of chromium as well as specific solvent will vary depending on the particular 9α-halo steroid (I) used, the amount of oxygen remaining after degassing, the particular chromium salt, the scale used, etc as is well known to those skilled in the art.

The use of the 11β-hydroxy steroids (II) are well known to those skilled in the art.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula CH$_3$—C(=Z$_1$)H. Groups R$_i$ and R$_j$ would represent monovalent variable substituents if attached to the formula CH$_3$—CH$_2$—C(R$_i$)(R$_j$)H$_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both R$_i$ and R$_j$ are bonded to the preceding carbon atom. Also, for any molecule with an established system of carbon atom numbering, such as steroids, these carbon atoms are designated as C$_i$, where "i" is the integer corresponding to the carbon atom number. For example, C$_6$ represents the 6 position or carbon atom number in the steroid nucleus as traditionally designated by those skilled in the art of steroid chemistry. Likewise the term "R$_6$" represents a variable substituent (either monovalent or bivalent) at the C$_6$ position.

Chemical formulas or portions thereof drawn in a linear fashion represent atoms in a linear chain. The symbol "—" in general represents a bond between two atoms in the chain. Thus CH$_3$—O—CH$_2$—CH(R$_i$)—CH$_3$ represents a 2-substituted-1-methoxypropane compound. In a similar fashion, the symbol "=" represents a double bond, e.g., CH$_2$=C(R$_i$)—O—CH$_3$, and the symbol "≡" represents a triple bond, e.g., HC≡C—CH(R$_i$)—CH$_2$—CH$_3$. Carbonyl groups are represented in either one of two ways: —CO— or —C(=O)—, with the former being preferred for simplicity.

A cyclic (ring) structure for any compound herein defines an orientation with respect to the plane of the ring for substituents attached to each carbon atom of the cyclic compound. In formulas depicting such compounds, a substituent attached to a carbon atom below the plane of the ring is identified as being in the alpha (α) configuration and is indicated by a broken, dashed or dotted line attachment to the carbon atom, i.e., by the symbol "— — —" or "...". The corresponding substituent attached above the plane of the ring is identified as being in the beta (β) configuration. When a variable substituent is bivalent, the valences may be taken together or separately or both in the definition of the variable. For example, a variable R$_i$ attached to a carbon atom as —C(=R$_i$)— might be bivalent and be defined as oxo or keto (thus forming a carbonyl group (—CO—) or as two separately attached monovalent variable substituents α-R$_{i-j}$ and β-R$_{i-k}$. When a bivalent variable, R$_i$, is defined to consist of two monovalent variable substituents, the convention used to define the bivalent variable is of the form "α-R$_{i-j}$:β-R$_{i-k}$" or some variant thereof. In such a case both $\alpha\text{-}R_{i\text{-}j}$ and $\beta\text{-}R_{i\text{-}k}$ are attached to the carbon atom to give $-C(\alpha\text{-}R_{i\text{-}j})(\beta\text{-}R_{i\text{-}k})-$. For example, when the bivalent variable $R_6$, $-C(=R_6)-$ is defined to consist of two monovalent variable substituents, two monovalent variable substituents are $\alpha\text{-}R_{6\text{-}1}:\beta\text{-}R_{6\text{-}2} \ldots \alpha\text{-}R_{6\text{-}9}:\beta\text{-}R_{6\text{-}10}$, etc, giving $-C(\alpha\text{-}R_{6\text{-}1})(\alpha\text{-}R_{6\text{-}2})-, \ldots -C(\alpha\text{-}R_{6\text{-}9})(\beta\text{-}R_{6\text{-}10})-$, etc. Likewise, for the bivalent variable $R_{11}$, $-C(=R_{11})-$, two monovalent variable substituents are $\alpha\text{-}R_{11\text{-}1}:\beta\text{-}R_{11\text{-}2}$. For a ring substituent for which separate $\alpha$ and $\beta$ orientations do not exist (e.g. due to the presence of a carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula $-C_1(R_i)H-C_2(R_j)H-$ ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa $(-O-)$ and the formula thereby describes an epoxide. When $R_i$ and $R_j$ are taken together to form a more complex entity, such as the group $-X-Y-$, then the orientation of the entity is such that $C_1$ in the above formula is bonded to X and $C_2$ is bonded to Y. Thus, by convention the designation "... $R_i$ and $R_j$ are taken together to form $-CH_2-CH_2-O-CO-\ldots$" means a lactone in which the carbonyl is bonded to $C_2$. However, when designated "... $R_j$ and $R_i$ are taken together to form $-CH_2-CH_2-O-CO-$ the convention means a lactone in which the carbonyl is bonded to $C_1$.

The carbon atom content of variable substituents is indicated in one of two ways. The first method uses a prefix to the entire name of the variable such as "$C_1-C_4$", where both "1" and "4" are integers representing the minimum and maximum number of carbon atoms in the variable. The prefix is separated from the variable by a space. For example, "$C_1-C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2-C_4$ alkoxycarbonyl describes a group $CH_3-(CH_2)_n-O-CO-$ where n is zero, one or 2. By the second method the carbon atom content of only each portion of the definition is indicated separately by enclosing the "$C_iC_j$" designation in parentheses and placing it immediately (no intervening space) before the portion of the definition being defined. By this optional convention ($C_1-C_3$) alkoxycarbonyl has the same meaning as $C_2-C_4$ alkoxycarbonyl because the "$C_1-C_3$" refers only to the carbon atom content of the alkoxy group. Similarly while both $C_2-C_6$ alkoxyalkyl and ($C_1-C_3$) alkoxy($C_1-C_3$) alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. DEFINITIONS

All temperatures are in degrees Centigrade.
TLC refers to thin-layer chromatography.
THF refers to tetrahydrofuran.
THP refers to tetrahydropyranyl.
DMF refers to dimethylformamide.
DMAC refers to dimethylacetamide.
Halo refers to $-Cl$ and $-Br$.
Thioglycolic acid or thiovanic acid refers to $HS-CH_2-COOH$.
HPLC refers to high-pressure liquid chromatography.
HPLC conditions reported are relative area percent; 10 cm, 5$\mu$, Neucleosil C-18, mobile phase acetonitrile/water (45/55).
When solvent pairs are used, the ratios of solvents used are volume/volume (v/v).
DMSO refers to dimethylsulfoxide.
DMI refers to 1,3-dimethyl-2-imidazolidinone.
Chromium ion includes both chromium (II) and chromium (III).
Soluble does not refer to theoretical solubility where a solute may be finitely and infinitesimally soluble in a solvent, but rather refers to practical, useful or sufficiently soluble as normally used by one skilled in the art.
The term 9$\alpha$-halo steroid (I) includes the compounds of (IA).
The term 11$\beta$-hydroxy steroid (II) includes the compounds of (IIA).
Chemical yield refers to the isolated yield.
Yield refers to percent product made but not necessarily isolated.
$R_t$ is
$C_1-C_5$ alkyl,
$\phi$ optionally substituted with
  $-OH$,
  $-OR_1$ where $R_1$ is $C_1-C_3$ alkyl,
  $-SR_1$,
  $-CO-R_2$ where $R_2$ is $C_1-C_3$ alkyl or $\phi$,
  $-COOH$,
  $-COOR_2$ where $R_2$ is as defined above
  $-(CH_2)_n-\phi$ where n is from 1 through 5 and $\phi$ is as defined above,
  $-CH_2-COOH$,
  $-CH_2CH_2-COOH$.
NMR refers to nuclear (proton) magnetic resonance spectroscopy, chemical shifts are reported in ppm ($\delta$) downfield from tetramethylsilane.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

9$\alpha$-Bromo-11$\beta$,17$\alpha$,21-trihydroxypregn-4-ene-3,20-dione 21-acetate (I)

Tetrafluoroboric acid (50%, 8.0 ml) is added to a slurry of 17$\alpha$,21-dihydroxypregna-4,9(11)-diene-3,20-dione 21-acetate ((U.S. Pat. No. 3,005,834, Example 1, 30.97 g) in acetone (180 ml) and water (7.7 ml) and the temperature is adjusted to 2°. A slurry of dibromodimethylhydantoin (14.71 g) in water (30 ml) is then added followed by a acetone (10 ml) rinse. The temperature rises to 8° and the slurry is recooled to 2°. After 4 hr stirring, TLC indicates the disappearance of the Δ9(11) steroid starting material. The product slurry is diluted with the dropwise addition of water (250 ml) over 16 min. The slurry is cooled to −10° and the product collected by filtration, washed with water (3×100 ml) and partially air-dried to provide the title compound.

PREPARATIONS 2–5

Following the general procedure of PREPARATION 1 and making noncritical variations but starting with the appropriate $\Delta^{9(11)}$-steroid, the following bromohydrins are obtained

PREPARATION 2

9α-Bromo-11β-hydroxyandrost-4-ene-3,17-dione (I)

PREPARATION 3

9α-Bromo-11β,17α,21-trihydroxypregna-1,4-diene-3,20-dione 21-acetate (I)

PREPARATION 4

9α-Bromo-11β,16α,17α,21-tetrahydroxypregna-1,4-diene-3,20-dione 21-acetate (I)

PREPARATION 5

9α-Bromo-6α-fluoro-11β,17α,21-trihydroxy-16α-methylpregna-1,4-diene-3,20-dione 21-acetate (I)

EXAMPLE 1

11β,17α,21-Trihydroxypregn-4-ene-3,20-dione 21-acetate (II)

9α-Bromo-11β,17α,21-trihydroxypregn-4-ene-3,20-dione 21-acetate (I, PREPARATION 1, 49.52 g) is dissolved in acetone (53 ml) and DMF (95 ml) at 50° and is purged free of oxygen by alternating vacuum and nitrogen. This mixture is added dropwise over 1.5 hr to a slurry of chromic chloride hexahydrate (1.07 g), zinc dust (7.84 g) and thiovanic acid (11.2 ml) in acetone (112 ml) which was degassed as described above. The temperature during the addition is maintained at about 2° and then, 20 min. after the addition, the temperature is slowly (2.2 hr) elevated to 54°. LC analysis (relative area %) at this point shows the reaction is complete. The acetone is removed by vacuum distillation and the resulting slurry is treated with water (316 ml). The slurry is cooled to −10° and after 1 hr, the solids are collected by vacuum filtration, washed with water (3×100 ml) and air-dried to constant weight to give the product containing some unreacted zinc. The zinc is removed by slurring the solids in warm methylene chloride/methanol (2/1) and filtering. The product is isolated from the filtrate by adding water and collecting the precipitate by vacuum filtration. The solids are washed with cold methanol and dried in a vacuum oven at 60° to give the title compound, TLC $R_f$=0.37 (methanol/chloroform, 5/95); HPLC 98.4% (II), 1.2% $\Delta^{9(11)}$.

EXAMPLE 2

11β-Hydroxyandrost-4-ene-3,17-dione (II)

9α-Bromo-11β-hydroxyandrost-4-ene-3,17-dione (I, PREPARATION 2, 2.134 g) is dissolved in THF (THF 20ml) and degassed as described in EXAMPLE 1. This solution is added dropwise over 20 min to a freshly degassed slurry of chromic chloride hexahydrate (81 mg), thiovanic acid (0.70 ml) and zinc dust (555 mg) in DMF (4 ml) at 0° THF (about 8 ml) is used for rinse purposes. The slurry is stirred at 0° to 2° for 2.2 hr and then is slowly heated to 50°. The THF is removed by vacuum distillation and the remaining slurry is diluted with ethyl acetate (25 ml) and water (25 ml). The unreacted zinc is removed by filtration and is washed with aqueous ethyl acetate. The combined filtrate and wash is allowed to separate. The organic layer is washed with water (3×25 ml) and finally is concentrated under vacuum to a residue. The residue is recrystallized from 1 part toluene and 2 parts heptane to give the title compound, TLC $R_f$=0.45 (methanol/methylene chloride, 5/95); HPLC 96.7% (II), 2.9% $\Delta^{9(11)}$.

EXAMPLE 3

11β,17α,21-Trihydroxypregna-1,4-diene-3,20-dione 21-acetate (II)

A slurry of zinc dust (1.120 g), chromic chloride hexahydrate (135 mg) and thiovanic acid (1.4 ml) in DMF (10 ml) is degassed as described in EXAMPLE 1. The temperature is adjusted to 2°. To this mixture is added dropwise over 1.0 hr a degassed solution of 9α-bromo-11β,17α,21-trihydroxypregna-1,4-diene-21-acetate (I, PREPARATION 3, 4.815 g) in THF (25 ml) and methylene chloride (25 ml). Two ml of THF is used as a rinse. The slurry is stirred at 2° for 2 hr and then at 23° for 2.5 days. Most of the THF and methylene chloride are removed by vacuum distillation at 43°–47°. The remaining slurry is diluted with water (60 ml) added dropwise over 20 min. After cooling the slurry to 3°, the product is isolated by filtration and is washed thoroughly with water. The solids are air-dried and then recrystallized from acetone to give the title compound, TLC $R_f$=0.21 (hexane/acetone/methylene chloride, 30/20/50); HPLC 97.2% (II), 1.1% $\Delta^{9(11)}$, 1.0% starting material.

EXAMPLE 4

11β,16α,17α,21-Tetrahydroxypregna-1,4-diene-3,20-dione 21-acetate (II)

Following the general procedure of EXAMPLE 3 and making noncritical variations, 9α-bromo-11β,16α,17α,21-tetrahydroxypregna-1,4-diene-3,20-dione 21-acetate (I, PREPARATIO ml) and DMF (8 ml) is added over 0.5 hr to a slurry of chromium III (135 mg), zinc dust (1.11 g) and thiovanic acid (1.40 ml) in DMF (8 ml) 8 ml at 0°. After stirring the slurry at 0° for 2 hr, the temperature is gradually raised to 45°. Then water (40 ml) is added over 1.1 hr and the thick slurry that develops is recooled to 0°. After 1.0 hr, the product is collected by vacuum filtration, washed thoroughly with water and air-dried. This residue is recrystallized after removal of the unused zinc, from a 2-phase system of aqueous methanol and methylene chloride. The solids are isolated by filtration and are washed with water and vacuum oven dried to give the title compound, TLC $R_f$=0.44 (methanol/chloroform, 5/95); HPLC 97.0% (II), 2.0% $\Delta^{9(11)}$.

EXAMPLE 5

6α-Fluoro-11β,17α,21-trihydroxy-16α-methylpregna-1,4-diene-3,20-dione 21-acetate (II)

To a freshly degassed slurry of chromic chloride hexahydrate (26 mg), zinc dust (113 mg) and thiovanic acid (0.14 ml) in DMF (4 ml) is added, over 12 min, a degassed solution of 9α-bromo-6α-fluoro11β,17α,21-trihydroxy-16α-methylpregna-1,4-diene-3,20-dione 21-acetate (I, PREPARATION 5, 516 mg) in THF (12 ml) and methylene chloride (4 ml). The temperature is maintained at 0° during this addition and for another 1.8 hr. The slurry is then warmed to 40° and concentrated by vacuum distillation. Water (25 ml) is added over 15 rain at about 20°. After cooling the slurry to 0°, the solids are collected, washed with water and dried to give a residue. The residue is dissolved in acetone at reflux and the zinc is removed by filtration. Water is added to the filtrate to precipitate product. After cooling the slurry to 0°, the solids are collected, washed with aqueous acetone and dried to give the title compound, TLC $R_f$=0.46 (methanol/chloroform, 5/95); HPLC 88.2% (II), 0.6% $\Delta^{9(11)}$, 1.9% starting material.

EXAMPLES 6–15

11β-Hydroxyandrost-4-ene-3,17-dione (II)

See Table 1 in CHART B.

A solution of the chromium salt (0.2 mmol) in thiovanic acid (1.5 ml) and DMF (28 ml) is prepared. When chromium sulfate is used, water (2.0 ml) is added, unless specified otherwise. This solution is degassed by alternating nitrogen purge and evacuation. To this solution is added zinc dust (222 mg) followed by a freshly degassed solution of 9α-bromo-11β-hydroxyandrost-4-ene-3,17-dione (I, PREPARATION 2, 1 mmole) in DMF (10 ml). The bromohydrin solution is added all at once or dropwise over the specified period and specified temperature. Periodically, 10 λ samples of the reaction slurry were withdrawn, diluted with aqueous acetonitrile and analyzed by HPLC. All the reductions were carried out to >70% completion. The 11β-hydroxy and $\Delta^{9(11)}$ compounds are the only products produced and the values given in TABLE 1 (CHART B) are normalized relative area percents.

EXAMPLE 16

11β,17α,21-Trihydroxypregn-4-ene-3,20-dione 21-acetate (II)

9α-Bromo-11β,17α,21-trihydroxypregn-4-ene-3,20-dione 21-acetate (I, PREPARATION 1, 65 kg), acetone (75 l) and DMF (176 l) are combined at 30° (for less than 30 min) and then cooled to 20–25°. Chromic chloride (1.87 kg) acetone (90 l), DMF (26 l) and thovanic acid (19.14 kg) are combined and stirred. Zinc powder (6.75 kg) and acetone (12 l) are slurried. The zinc slurry is added to the chromium mixture, rinsing with acetone (2×6 l). The zinc/chromium mixture is cooled to 0° and degassed. The steroid mixture is then added to the zinc/chromium mixture over a period of 1 hr with a resulting exotherm. The reaction mixture is maintained at 0° and is monitored by TLC. When complete, the reaction mixture is warmed to 35°, and water (550 l) is added followed by cooling to 0°. The mixture is filtered and the cake rinsed with water (3×180 l) and cold (−20°) methanol (2×110 l). The cake is dissolved in methylene chloride (330 l), methanol (165 l) and acetic acid (0.26 kg) under reflux for 3 hr. The mixture is then cooled to 30°. Methylene chloride (2×30 l) and methanol (2×15 l) is added to form a slurry. Methanol (165 l) is added followed by distillation to 64° and 350 l. The mixture is filtered and cake washed with cold (0°) methanol (147 l) to obtain the title compound.

EXAMPLE 17

11β,16α,17α,21-Tetrahydroxypregna-1,4-diene-3,20-dione 21-acetate (II)

Following the general procedure of EXAMPLE 6 and making noncritical variations but starting with 9α-bromo-11β,16α,17α,21-tetrahydroxypregna-1,4-diene-3,20-dione 21-acetate (I) but using 0.05 equivalents of chromium (II) the title compound is obtained in 90.5% chemical yield.

EXAMPLE 18

11β,16α,17α,21-Tetrahydroxypregna-1,4-diene-3,20-dione 21-acetate (II)

Following the general procedure of EXAMPLE 6 and making noncritical variations but starting with 9α-bromo-11β,16α,17α,21-tetrahydroxypregna-1,4-diene-3,20-dione 21-acetate (I) but using 0.1 equivalents of chromium (II) the title compound is obtained in 96.8% chemical yield.

EXAMPLE 19

11β,17α,21-Trihydroxy-6α-methylpregna-1,4-diene-3,20-dione 21-acetate (II)

Following the general procedure of EXAMPLES 3–5, 17 and 18 and making non-critical variations but starting with 9α-bromo-11β,17α,21-trihydroxy-6α-methylpregna-1,4-diene-3,20-dione 21-acetate (I), the title compound is obtained.

EXAMPLE 20

11β,17α,21-Trihydroxypregn-4-ene-3,20-dione 21-acetate (II)

Following the general procedure of EXAMPLES 1, 2 and 6–16 and making non-critical variations but starting with 9α-chloro-11β,17α,21-trihydroxypregn-4-ene-3,20-dione 21-acetate (I), the title compound is obtained.

EXAMPLE 21

11β,17α,21-Trihydroxypregna-1,4-diene-3,20-dione 21-acetate (II)

Following the general procedure of EXAMPLE 3–5, 17 and 18 and making non-critical variations but starting with 9α-chloro-11β,17α,21-trihydroxypregna-1,4-diene-3,20-dione 21-acetate (I), the title compound is obtained.

EXAMPLE 22

11β,17α,21-Trihydroxy-6α-methylpregna-1,4-diene-3,20-dione 21-acetate (II)

Following the general procedure of EXAMPLES 3–5, 17 and 18 and making non-critical variations but starting with 9α-chloro-11β,17α,21-trihydroxy-6α-methylpregna-1,4-diene-3,20-dione 21-acetate (I), the title compound is obtained.

EXAMPLES 23–27

Following the general procedure of EXAMPLES 1, 2 and 6–16 and making non-critical variation and starting with the corresponding 9α-halo steroid (I) the following 11β-hydroxy steroids (II) are obtained:

EXAMPLE 23

6α-Fluoro-11β,16α,17α,21-tetrahydroxypregn-4-ene-3,20-dione 21-acetate

EXAMPLE 24

6α-Fluoro-11β,16α,17α,21-tetrahydroxypregn-4-ene-3,20-dione 21-acetate 16,17-acetonide

EXAMPLE 25

11β,17α,21-Trihydroxypregn-4-ene-3,20-dione

EXAMPLE 26

11β,17α,21-Trihydroxy-6α-methylpregn-4-ene-3,20-dione 21-acetate

EXAMPLES 27–29

Following the general procedure of EXAMPLES 3–5, 17 and 18 and making non-critical variation and starting with the corresponding 9α-halo steroid (I) the following 11β-hydroxy steroids (II) are obtained:

EXAMPLE 27

6α-Fluoro-11β,21-dihydroxy-16α-methylpregna-1,4-diene-3,20-dione 21-acetate

EXAMPLE 28

6α-Fluoro-11β,16α,17α,21-tetrahydroxypregna-1,4-diene-3,20-dione 21-acetate 16,17-acetonide

EXAMPLE 29

6α-Fluoro-11β,17α,21-trihydroxypregna-1,4-diene-3,20-dione 21-acetate

EXAMPLE 30

11β,17α,21-Trihydroxy-6α-methylpregna-1,4-diene-3,20-dione 21-acetate (II)

Following the general procedure of EXAMPLE 6 and making noncritical variations but starting with 9α-bromo-11β,17α,21-trihydroxy-6α-methylpregna-1,4-diene-3,20-dione 21-acetate (I) and using 0.10 equivalents of chromic chloride, the title compound is obtained in 96% overall yield from the corresponding $\Delta^{9(11)}$ starting material. The retention time on HPLC and the signals in the NMR fit for the title compound.

EXAMPLE 31

11β,17α,21-Trihydroxypregn-4-ene-3,20-dione (II)

Following the general procedure of EXAMPLE 6 and making noncritical variations but starting with 9α-bromo-11β,17α,21-hydroxypregn-4-ene-3,20-dione and using 0.10 equivalents of chromic chloride, the title compound is obtained in 96% overall yield from the corresponding $\Delta^{9(11)}$ starting material. The retention times on both TLC and HPLC were the same as for a known sample of the title compound hydrocortisone.

EXAMPLE 32

11β,16α,17α,21-Tetrahydroxypregna-1,4-diene-3,20-dione 21-acetate (II)

Following the general procedure of EXAMPLE 1 and making noncritical variations but starting with 9α-bromo-11β,16α,17α,21-tetrahydroxypregna-1,4-diene-3,20-dione 21-acetate (I, PREPARATION 4, 72 Kg) in DMF (164.2 l) is added to a slurry of chromic chloride (5.4 kg), zinc dust (6.6 kg) and thiovanic acid (18.6 kg) in DMF (47 kg) and DMSO (33.0 l). The product is isolated and purified following the general procedure of EXAMPLE 4 to provide 47 Kg of the title compound.

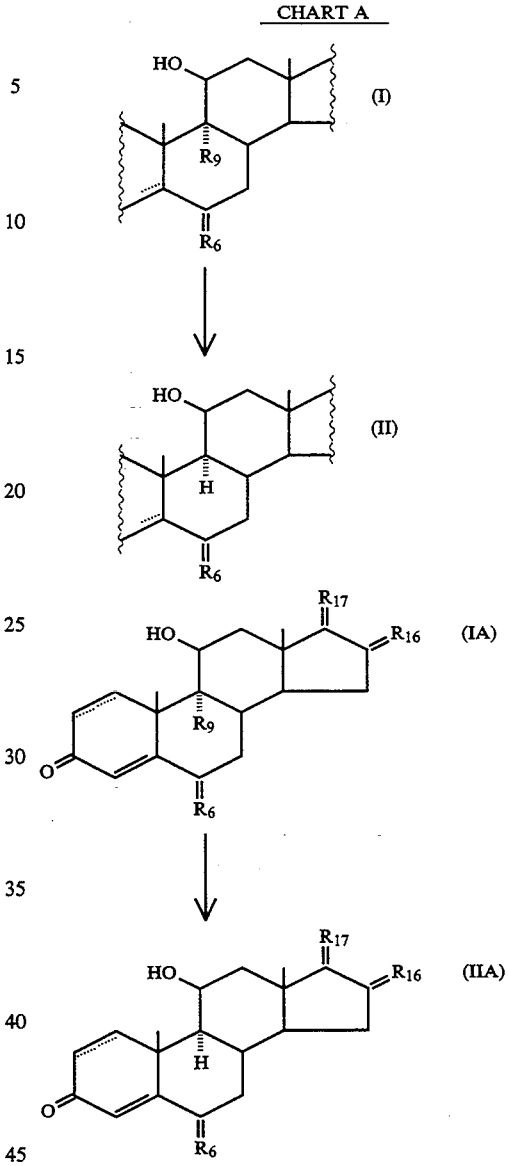

CHART A

CHART B

TABLE 1

| EXAMPLE | Cr Salt | Order[1] | T | 11β-OH | $\Delta^{9(11)}$ | time |
|---|---|---|---|---|---|---|
| 6 | sulfate[2] | O | 20–25° | 78.1 | 21.9 | 6 days |
| 7 | none | O | 20–25° | 81.9 | 18.1 | 10–20 hr |
| 8 | sulfate | O | 20–25° | 87.9 | 12.1 | 1–2 hr |
| 9 | chloride | O | 20–25° | 97.7 | 2.3 | 40 min |
| 10 | sulfate | R[3] | 20–25° | 90.6 | 9.4 | 2 hr |
| 11 | chloride | R[4] | 20–25° | 100 | none | 24 min |
| 12 | chloride | R[5] | 20–25° | 99.3 | 0.7 | 20 min |
| 13 | sulfate | R[6] | 20–25° | 95.4 | 4.6 | >10 hr |
| 14 | chloride[7] | R | 20–25° | 96.7 | 3.3 | >2.5 hr |
| 15 | chloride[8] | R | 20–25° | 99.2 | 0.8 | 2.0 hr |

[1] "O" refers to Old order of addition of reactants where the 9α-halo steroid (I) was not added last; "R" refers to Reverse order of addition where 9α-halo steroid (I) is added last
[2] no water
[3] 9α-steroid (I) added over 15 min
[4] 9α-steroid (I) added over 23 min
[5] 9α-steroid (I) added over about 1 min
[6] 9α-steroid (I) added over 9 hr
[7] 1 equivalent thiol, chromium reduced to 0.1 equivalents
[8] 1.8 equivalents thiol, chromium reduced to 0.1 equivalents

We claim:

1. A process for the preparation of an 11β-hydroxy steroid of formula (IIA)

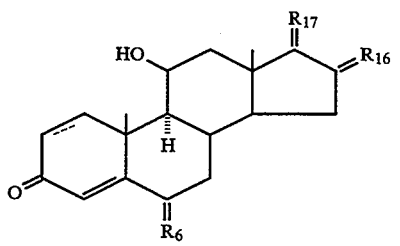

where ⁼⁼⁼ is a single or double bond;
where $R_6$ is $\alpha$-$R_{6-1}$:$\beta$-$R_{6-2}$, where one of $R_{6-1}$ and $R_{6-2}$ is —H and the other is —H, —F or —CH$_3$;
where (D-I) $R_{16}$ is $\alpha$-$R_{16-1}$:$\beta$-$R_{16-2}$ where one of $R_{16-1}$ and $R_{16-2}$ is —H and the other is —H, —OH or —CH$_3$ and $R_{17}$ is

=O, $\alpha$—H:$\beta$—CO—CH$_3$, $\alpha$—OR$_{17-5}$:$\beta$—CO—CH$_3$ where R$_{17-5}$ is —H or —CO—R$_{17-51}$ where R$_{17-51}$ is C$_2$—C$_4$ alkyl or —$\phi$ optionally substituted with 1 or 2 —OCH$_3$, $\alpha$—OR$_{17-1}$:$\beta$—CO—CH$_2$—OR$_{21-1}$ where R$_{17-1}$ is —H or —CO—R$_{17-2}$ where R$_{17-2}$ is C$_1$—C$_3$ alkyl or —$\phi$ and where R$_{21-1}$ is —H or —CO—R$_{21-2}$ where R$_{21-2}$ is C$_1$—C$_3$ alkyl or —$\phi$ optionally substituted with —Cl or —NO$_2$, $\alpha$—OR$_{17-3}$:$\beta$—CN where R$_{17-3}$ is

—H,

THP,

—CH$_2$—OCH$_3$,

—CHR$_{17-31}$—O—R$_{17-32}$ where R$_{17-31}$ is C$_1$—C$_3$ alkyl and R$_{17-32}$ is C$_1$—C$_4$ alkyl or —$\phi$ and —SiR$_{17-33}$R$_{17-34}$R$_{17-35}$ where R$_{17-33}$, R$_{17-34}$ and R$_{17-35}$ are the same or different and are selected from the group consisting of C$_1$—C$_4$ alkyl, C$_1$—C$_4$ alkoxy, C$_1$—C$_4$ monohaloalkyl where halo is —Br or —Cl, —$\phi$ optionally substituted with 1 or 2 —OCH$_3$ or —NH$_2$;

where (D-II) the 16,17-acetonide of a compound where R$_{16-1}$ is —OH, and where R$_{17}$ is $\alpha$-OR$_{17-1}$:$\beta$—CO—CH$_2$—OR$_{21-1}$ where R$_{17-1}$ is —H where R$_{21-1}$ is as defined above which comprises (1) contacting a 9$\alpha$-halo steroid of formula (IA)

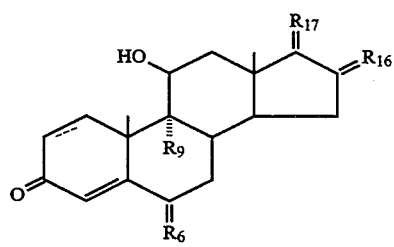

where R$_9$ is —Cl or —Br with <1 equivalent of chromium ion (II) or (III), a hydrogen radical source and a means for reducing the chromium (III) to chromium (II) where all the reactants are in solution in the solvent, co-solvent or mixture of solvents used, where R$_6$, R$_{16}$, R$_{17}$ and ⁼⁼⁼ are as defined above.

2. A process according to claim 1 where ⁼⁼⁼ is a double bond.

3. A process according to claim 1 where R$_{17}$ is $\alpha$-OR$_{17-1}$:$\beta$—CO—CH$_2$—OR$_{21-1}$.

4. A process according to claim 1 where ⁼⁼⁼ is a single bond and R$_{17}$ is =O, $\alpha$-OR$_{171}$:$\beta$—CO—CH$_2$—OR$_{21-1}$, $\alpha$-H:$\beta$—CO—CH$_3$ or $\alpha$-OR$_{17-5}$:$\beta$—CO—CH$_3$ and $\alpha$-OR$_{17-3}$:$\beta$—CN.

5. A process according to claim 1 where the 9$\alpha$-halo steroid (I) is added to the chromium ion.

6. A process according to claim 1 where there is sufficient water as co-solvent present to solubilize the chromium ion if not solubilized by the solvent or solvent mixture.

7. A process according to claim 1 where 9$\alpha$-halo steroid (I) is slowly added to the chromium ion.

8. A process according to claim 1 where the hydrogen radical source is selected from the group consisting of hypophosphofous acid, 1,4-dihydrobenzene, 1-benzyl-1,4-dihydronicotinamide, cyclopentadiene, catechol, thiols, H—Si(R)$_3$ where the R's are the same or different and are selected from the group consisting of C$_1$—C$_4$ alkyl and —$\phi$ optionally substituted with 1 or 2 —OCH$_3$, and H—Sn(R)$_3$ where R is as defined above.

9. A process according to claim 1 where >1 equivalent of hydrogen radical source is used.

10. A process according to claim 1 where the means for reducing chromium (III) to chromium (II) is selected from the group consisting of zinc, magnesium, zinc amalgam and magnesium amalgam.

11. A process according to claim 1 where the 11β-hydroxy steroid (II) is

11β,17α,21-trihydroxypregn-4-ene-3,20-dione 21-acetate,

11β-hydroxyandrost-4-ene-3,17-dione,

11β,17α,21-trihydroxypregna-1,4-diene-3,20-dione 21-acetate,

11β,16α,17α,21-tetrahydroxypregna-1,4-diene-3,20-dione 21-acetate,

6α-fluoro-11β,17α,21-trihydroxy-16α-methylpregn-1,4-diene-3,20-dione 21-acetate, 11β-16α,17α,21-tetrahydroxypregn-1,4-diene-3,20-dione 21-acetate 11β,17α, 21-trihydroxy-6α-methylpregna-1,4-diene-3,20-dione 21-acetate, 6α-fluoro-11β,16α,17α,21-trihydroxypregn-4-ene-3,20-dione 21-acetate, 6α-fluoro-11β,16α,17α,21-tetrahydroxypregn-4-ene-3,20-dione 21-acetate 16,17-acetonide, 11β,17α,21-trihydroxypregn-4-ene-3,20-dione, 11β,17α,21-trihydroxy-6α-methylpregn-4-ene-3,20-dione 21-acetate, 6α-fluoro-11β,21-dihydroxy-16α-methylpregna-1,4-diene-3,20-dione 21-acetate, 6α-fluoro-11β,16α,17α,21-tetrahydroxypregna-1,4-diene-3,20-dione 21-acetate 16,17-acetonide or 6α-fluoro-11β,16α,17α,21-trihydroxypregna-1,4-diene-3,20dione 21-acetate.

12. A process for the preparation of an 11β-hydroxy steroid of formula (IIA)

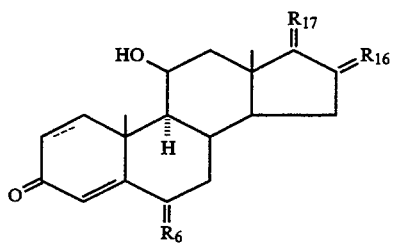

(IIA)

where R$_6$ is α-R$_{6-1}$:β-R$_{6-2}$, where one of R$_{6-1}$ and $_{6-2}$ is —H and the other is —H, —F or —CH$_3$;
where     is a single or double bond;
where R$_6$ is α-R$_{6-1}$:β-R$_{6-2}$, where one of R$_{6-1}$ and R$_{6-2}$ is —H and the other is —H, —F or —CH$_3$;
where (D-I) R$_{16}$ is α-R$_{16-1}$:β-R$_{16-2}$ where one of R$_{16-1}$ and R$_{16-2}$ is —H and the other is —H, —OH or —CH$_3$ and R$_{17}$ is
=O,
α-H:β—CO—CH$_3$,
α-OR$_{17-5}$:β—CO—CH$_3$ where R$_{17-5}$ is —H, —CO—R$_{17-51}$ where R$_{17-51}$ is C$_2$—C$_4$ alkyl or —ϕ optionally substituted with 1 or 2 —OCH$_3$,
α-OR$_{17-1}$:β—CO—CH$_2$—OR$_{21-1}$ where R$_{17-1}$ is —H or —CO—R$_{17-2}$ where R$_{17-2}$ is C$_1$—C$_3$ alkyl or —ϕ and where R$_{21-1}$ is —H or —CO—R$_{21-2}$, where R$_{21-2}$ is C$_1$—C$_3$ alkyl or —ϕ optional substituted with —Cl or —NO$_2$,
α-OR$_{17-3}$:β—CN where R$_{17-3}$ is
—H,
THP,
—CH$_2$—OCH$_3$,
—CHR$_{17-31}$—O—R$_{17-32}$ where R$_{17-31}$ is C$_1$—C$_3$ alkyl and R$_{17-32}$ is C$_1$—C$_4$ alkyl or —ϕ and
—SiR$_{17-33}$R$_{17-34}$R$_{17-35}$ where R$_{17-33}$, R$_{17-34}$ and R$_{17-35}$ are the same or different and are selected from the group consisting of C$_1$—C$_4$ alkyl, C$_1$—C$_4$ alkoxy, C$_1$—C$_4$ monohaloalkyl where halo is —Br or —Cl, —ϕ optionally substituted with 1 or 2 —OCH$_3$ or —NH$_2$;
where (D-II) the 16,17-acetonide of a compound where R$_{16-1}$ is —OH, and where R$_{17}$ is α-OR$_{17-1}$:β—CO—CH$_2$—OR$_{21-1}$ where R$_{17-1}$ is —H where R$_{21-1}$ is as defined above which comprises
(1) adding a 9α-halo steroid of formula (IA)

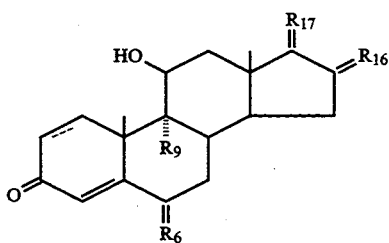

(IA)

where R$_9$ is —Cl or —Br to a mixture of <1 equivalent of chromium ion (II) or (III), a hydrogen radical source and a means for reducing chromium (III) to chromium (II) where all the reactants are in solution in the solvent, co-solvent or mixture of solvents used, where R$_6$, R$_{16}$, R$_{17}$ and ⁓ are as defined above.

13. A process according to claim 12 where the 9α-halo steroid (I) is added slowly.

14. A process according to claim 12 where there is sufficient water (co-solvent) present to solubilize the chromium ion if not solubilized by the solvent or solvent mixture.

15. A process according to claim 12 where <1 equivalent of chromium ion is present.

16. A process according to claim 12 where the hydrogen radical source is selected from the group consisting of hypophosphorous acid, 1,4-dihydrobenzene, 1-benzyl-1,4-dihydronicotinamide, cyclopentadiene, catechol, thiols, H—Si—(R)$_3$ where the R's are the same or different and are selected from the group consisting of C$_1$—C$_4$ alkyl and —ϕ optionally substituted with 1 or 2 —OCH$_3$, and H—Sn—(R)$_3$ where R is as defined above.

17. A process according to claim 12 where >1 equivalent of hydrogen radical source is used.

18. A process according to claim 12 where the means for reducing chromium (III) to chromium (II) is selected from the group consisting of zinc, magnesium, zinc amalgam and magnesium amalgam.

19. A process according to claim 12 where the 11β-hydroxy steroid (II) is
11β,17α,21-trihydroxypregn-4-ene-3,20-dione 21-acetate,
11β-hydroxyandrost-4-ene-3,17-dione,
11β,17α,21-trihydroxypregna-1,4-diene-3,20-dione 21-acetate,
11β,16α,17α,21-tetrahydroxypregna-1,4-diene-3,20-dione 21-acetate,
6α-fluoro-11β,17α,21-trihydroxy-16α-methylpregna-1,4-diene-3,20-dione 21-acetate,
11β,16α,17α,21-tetrahydroxypregna-1,4-diene-3,20-dione 21-acetate,
11β,17α,21-trihydroxy-6α-methylpregna-1,4-diene-3,20-dione 21-acetate,
6α-fluoro-11β,16α,17α,21-tetrahydroxypregn-4-ene-3,20-dione 21-acetate,
6α-fluoro-11β,16α,17α,21-tetrahydroxypregn-4-ene-3,20-dione 21-acetate 16,17-acetonide,
11β,17α,21-trihydroxypregn-4-ene-3,20-dione,
11β,17α,21-trihydroxy-6α-methylpregn-4-ene-3,20-dione 21-acetate,
6α-fluoro-11β,21-dihydroxy-16α-methylpregna-1,4-diene-3,20-dione 21-acetate,
6α-fluoro-11β,16α,17α,21-tetrahydroxypregna-1,4-diene-3,20-dione 21-acetate 16,17-acetonide or
6α-fluoro-11β,17α,21-trihydroxypregna-1,4-diene-3,20-dione 21-acetate.

* * * * *